United States Patent [19]  [11] 3,966,483
Albright  [45] June 29, 1976

[54] METHOD OF FORMULATING SOLUTION CONTAINING DISPERSED NITROCELLULOSE

[75] Inventor: Jack W. Albright, Detroit, Mich.

[73] Assignee: Carpenter Chemical Company, Detroit, Mich.

[22] Filed: Mar. 24, 1975

[21] Appl. No.: 561,088

[52] U.S. Cl.............................. 106/171; 106/178; 106/195; 106/198
[51] Int. Cl.² .......................................... C08L 1/18
[58] Field of Search ............ 106/171, 195, 198, 178

[56] References Cited
UNITED STATES PATENTS
2,689,561    9/1954    Posnack.......................... 106/171 X

*Primary Examiner*—Theodore Morris
*Attorney, Agent, or Firm*—Krass and Young

[57] ABSTRACT

To formulate a nitrocellulose based protective skin covering a base material is first prepared constituting a low viscosity solution of castor oil and ether in alcohol. A thickener is formed employing a small amount of nitrocellulose solids and a plasticizer in an acetone and alcohol solution. The thickener is then thoroughly mixed with the base and the balance of nitrocellulose solids are mixed with these components.

1 Claim, No Drawings

METHOD OF FORMULATING SOLUTION CONTAINING DISPERSED NITROCELLULOSE

BACKGROUND OF THE INVENTION

1. Field of the Invention

This invention relates to ether and alcohol solutions of nitrocellulose useful in forming flexible cellulose film bandages which adhere to human skin, and more particularly to an improved method of preparing such solutions.

2. Prior Art

Alcohol and ether solutions of nitrocellulose, known generically as collodion, have been used for many years to form flexible film coverings which adhere directly to the skin to protect cuts, abrasions and the like. Various additives such as castor oil which slows the rate of evaporation of the solution and increases its adhesion to the skin, and acetone and other volatile solvents and plasticizers may be formulated with the solution to provide a material which is easy to apply to the skin and dries within a few seconds to form a smooth, flexible, highly tenacious coating. These coating solutions are termed court plaster.

The cellulose fibers must of course be homogeneously dispersed through the resulting solution. Because of the structure of the cellulose fibers and viscosity of the solution, it is difficult to obtain this dispersion and the material must be prepared on a batch basis and mixed for long periods of time. The long mixing time is required so that the solvents will have sufficient time to act upon the cellulose fibers to break them up and to cause the cellulose to be thoroughly dispersed within the solution. It was previously common for these solutions to be mixed for several days in order to obtain a smooth homogeneous solution.

SUMMARY OF THE INVENTION

The present invention is directed toward a specific formula for court plaster and a unique method of blending the ingredients which results in a composition having excellent properties as a court plaster and which is smooth and homogeneous. The method of formulating the material substantially reduces the mixing time with respect to the time required for the previous methods.

The method of the present invention broadly comprises first forming a volatile base solution of ether and castor oil in an ethyl alcohol by mixing these components together. Independently, a "thickener" is formed by mixing a small portion of the required nitrocellulose solids in an alcohol solution with acetone and a plasticizer. Approximately one part by volume of the thickener is then mixed in with one part by volume the first component and with about one part by volume of nitrocellulose solids in an alcohol solution. This mixing requires as little as 24 hours to achieve a smooth, homogeneous mixture.

EXAMPLE 1

A base is first prepared by mixing the following ingredients for approximately 25 minutes in a high speed blender:

5 gallons ethyl alcohol
3 gallons ether
¼ gallon eucalyptus oil
1 gallon castor oil The alcohol and ether act as volatile solvents for the nitrocellulose subsequently introduced. The ethanol may contain small percentages of ethyl acetate and/or rubber hydrocarbons. For example, Shellacol 1%, produced by Commercial Solvents Corporation, which contains 5% by volume ethyl acetate and 1% by volume of rubber hydrocarbon. The eucalptus oil has healing properties and the castor oil acts as a plasticizer for the nitrocellulose, slows down the rate of evaporation of the resulting mixture and increases adhesion of the mixture to the skin.

Next, three gallons of a thickener are prepared by independently mixing the following components:

30% by weight nitrocellulose solids
12.4% by weight ethyl alcohol
8.8% by weight dioctyl phthalate
48.8% by weight acetone The nitrocellulose solids are preferably 70% nitrocellulose and 30% alcohol solvent having a five second viscosity. The ethyl alcohol and acetone act as volatile solvents for the nitrocellulose and the dioctyl phthalate is a plasticizer.

The thickener is then mixed in with the base compound for approximately 30 minutes until a homogeneous mixture is formed.

Finally, 12 pounds of the 70% nitrocellulose and alcohol is added to the above mixture. The materials are then mixed for approximately 24 hours in a high speed blender, until a smooth homogeneous mixture is obtained.

The resulting material forms a protective dressing which will cover any small skin abrasions with a flexible water proof highly tenacious skin covering.

EXAMPLE 2

The base described in Example 1, above, is modified by using 1½ gallons of ether and 1 gallons of castor oil, with no eucalyptus oil, all other ingredeints are as above. The base, thickener and nitrocellulose are all mixed together.

Having thus described my invention, I claim:

1. The method of formulating a nitrocellulose based skin covering material comprising: blending a base consisting of about one part per volume of castor oil and three parts per volume of ether in five parts per volume of alcohol; preparing a thickener consisting of 30% by weight of 70% nitrocellulose solids with about 50% by weight acetone and 9% by weight plasticizer, with the balance alcohol; mixing one part by volume thickener to about three parts per volume of the base; and mixing 1 gallon part by volume of 70% nitrocellulose into the combined base and thickener.

* * * * *